US007407774B2

(12) United States Patent
Ebinuma et al.

(10) Patent No.: US 7,407,774 B2
(45) Date of Patent: Aug. 5, 2008

(54) METHOD FOR REDUCING INFLUENCE OF HEMOGLOBIN WITH ALBUMIN IN AN ASSAY

(75) Inventors: Hiroyuki Ebinuma, Ryugasaki (JP); Kumiko Yuki, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 0 days.

(21) Appl. No.: 11/684,827

(22) Filed: Mar. 12, 2007

(65) Prior Publication Data

US 2007/0154879 A1 Jul. 5, 2007

Related U.S. Application Data

(62) Division of application No. 10/764,455, filed on Jan. 27, 2004, now abandoned.

(51) Int. Cl.
*C12Q 1/26* (2006.01)

(52) U.S. Cl. .......................................... 435/25; 435/4

(58) Field of Classification Search .................. 435/25, 435/4

See application file for complete search history.

(56) References Cited

U.S. PATENT DOCUMENTS 3,791,933 A 2/1974 Moyer et al.
6,703,216 B2 * 3/2004 Parsons et al. ................ 435/25
6,811,998 B2 11/2004 Ghoshal et al.
2004/0063213 A1 * 4/2004 Hirai et al. .................... 436/87

FOREIGN PATENT DOCUMENTS

| | | |
|---|---|---|
| JP | 60-066993 | 4/1985 |
| JP | 60-168050 | 8/1985 |
| JP | 62-248500 | 10/1987 |
| JP | 9-84598 | 3/1997 |
| JP | 2001-197900 | 7/2001 |
| JP | 2001-292795 | 10/2001 |

OTHER PUBLICATIONS

Jeyasingham M. et al. Interaction Between Pryidine Nucleotide Coenzymes and Heme Proteins . . . Clinical Chemistry 35(10)2129-33, Oct. 1989.*

* cited by examiner

*Primary Examiner*—Ralph Gitomer
(74) *Attorney, Agent, or Firm*—Oblon, Spivak, McClelland, Maier & Neustadt, P.C.

(57) ABSTRACT

A method for quantitatively determining a specific component in a biological specimen, which includes reacting a biological specimen, in the presence of an electron acceptor, with an enzyme which has an ability, by the dehydrogenation reaction, to oxidize the specific component or a substance derived from the specific component, and measuring the formed reductant of the electron acceptor, wherein the method avoids the influence of hemoglobin effectively if any contained in the specimen by using a measuring reagent containing albumin, thereby making an quantitative determination of the target component accurately; and a reagent for the quantitative determination.

5 Claims, No Drawings

METHOD FOR REDUCING INFLUENCE OF HEMOGLOBIN WITH ALBUMIN IN AN ASSAY

This application is a Divisional Application of U.S. application Ser. No. 10/764,455, now abandoned.

FIELD OF THE INVENTION

The present invention relates to a method for quantitatively determining a specific component in a biological specimen, which comprises the steps of: reacting the biological specimen, in the presence of an electron acceptor, with an enzyme which has an ability, by the dehydrogenation reaction, to oxidize the specific component or a substance derived from the specific component, measuring the formed reductant of the electron acceptor and avoiding influence of hemoglobin, by which accurate quantitative determination can be made; and a reagent for quantitative determination.

BACKGROUND ART

For quantitatively determining a specific component in a biological specimens a method which comprises the steps of: reacting the biological specimen, in the presence of an electron acceptor, with an enzyme which has an ability, by the dehydrogenation reaction, to oxidize the specific component or a substance derived from the specific component, and measuring the formed reductant of the electron acceptor, by which the specific component in the biological specimen is indirectly quantitatively determined, has been known. Particularly, when a specific trace component is to be quantitatively determined, the method using a color developer having a higher color development sensitivity is also employed for detecting or quantitatively determining the formed reductant of the electron acceptor, in order to conduct the measurement with a higher sensitivity. For example, when NAD (nicotinamide adenine dinucleotide) or NADP (nicotinamide adenine dinucleotide phosphate) is used as the electron acceptor, its reductant i.e. NADH or NADPH is reacted with an electron carrier such as diaphorase, and a tetrazolium salt to form formazan for detection or quantitative determination.

However, the above quantitative determination methods are susceptible to other components in the biological specimen, for example, metal ions or metalloproteins. Particularly, when using a biological specimen in which hemoglobin, containing iron in the molecule, is included, there is a problem that accurate quantitative determination can not be conducted. For the influence of hemoglobin, there is change of absorption wavelength, which is caused by the hemoglobin being oxidized etc. Such reactions when observed during the measurement may cause errors in the measured values as a nonspecific reaction depending upon the measuring wavelength. Further, since hemoglobin protein has iron in the molecule, there is a possibility that electron transport system is inhibited.

Accordingly, various methods have been proposed as a method for avoiding the influence of hemoglobin in analysis or quantitative determination of the component contained in the test specimen. For example, JP-A-60-168050 discloses a clinical chemistry analysis method wherein a specific surfactant is added to the test specimen. JP-A-62-248500 discloses a reagent for measuring enzyme activity in serum containing thiourea. JP-A-9-84598 discloses a method wherein a reagent for measurement of enzyme activity which contains an inorganic salt sulfoxylate type reducing agent is used in measuring the activity of a specific enzyme in a specimen. JP-A-2001-292795 discloses a method wherein a nitrite is added to a reagent for measuring the concentration of an analyte contained in a hemoglobin-containing biological fluid, in order to suppress unwanted reaction between hemoglobin and a tetrazolium compound.

However, in a method for quantitatively determining a specific component in a biological specimen, which comprises reacting a biological specimen, in the presence of an electron acceptor, with an enzyme which has an ability, by the dehydrogenation reaction, to oxidize a specific component in a biological specimen or a substance derived from the specific component, and measuring the formed reductant of the electron acceptor, it is necessary to take into consideration not only the influence of change of the absorption wavelength of hemoglobin or influence of reducing properties thereof, but also inhibition of electron transport system. Accordingly, the influence of hemoglobin can not sufficiently be avoided even by the above-mentioned methods.

SUMMARY OF THE INVENTION

It is an object of the present invention to provide a method for quantitatively determining a specific component in a biological specimen, which comprises reacting the biological specimen, in the presence of an electron acceptor, with an enzyme which has an ability, by the dehydrogenation reaction, to oxidize the specific component or a substance derived from the specific component, and measuring the formed reductant of the electron acceptor, wherein the method avoids the influence of hemoglobin effectively if any contained in the specimen by using a measuring reagent containing albumin, thereby making an quantitative determination of the target component accurately; and a reagent for the quantitative determination.

The present inventors have conducted extensive studies to accomplish the above object, and as a result, found that a measuring reagent containing albumin enables a specific component in a biological specimen to be quantitatively determined accurately without being influenced by hemoglobin if any contained in the specimen, and further that this measuring reagent is effective as well in detecting the formed reductant of the electron acceptor with a color developer for quantitative determination. The present inventors have made the present invention based on this discovery.

The present invention provides a method for quantitatively determining a specific component in a biological specimen which comprises reacting a biological specimen, in the presence of an electron acceptor, with an enzyme which has an ability, by the dehydrogenation reaction, to oxidize the specific component or a substance derived from the specific component, and measuring the formed reductant of the electron acceptor, wherein a measuring reagent containing albumin is used.

According to the quantitative determination method of the present invention, a measuring reagent containing albumin can avoid the influence of hemoglobin if any contained in the specimen, and the target component can be quantitatively determined accurately.

The action mechanism of albumin in the quantitative determination method of the present invention is not clearly known. However, it is confirmed that the mechanism is not related to the change of the absorption wavelength of hemoglobin, and it is considered that the mechanism prevents electrons from being captured by hemoglobin in the electron transport system.

In the quantitative determination method of the present invention, it is preferred that the albumin is derived from human or bovine. According to this embodiment, influence of hemoglobin can be avoided efficiently.

Further, it is preferred to use a color developer for the measurement of the formed reductant of the electron acceptor, and the color developer is preferably a tetrazolium salt. According to these embodiments, even a slight amount of component can be quantitatively determined with a high sensitivity.

Further, the reductant of the electron acceptor is preferably NADH or NADPH. According to this embodiment, it is possible to avoid the influence caused by the change of absorption wavelength of hemoglobin.

The reagent for quantitative determination of a specific component in a biological specimen provided by the present invention specifically comprises albumin, an electron acceptor, and an enzyme which has an ability, by the dehydrogenation reaction, to oxidize the specific component or a substance derived from the specific component in the biological specimen. These components may be separated into two or more reagents, if necessary.

By using the reagent for quantitative determination of the present invention, the influence of hemoglobin if any contained in the test specimen can be avoided by the presence of albumin contained in the reagent, and the target component can be quantitatively determined accurately.

In the reagent for quantitative determination of the present invention, it is preferred that the albumin is derived from human or bovine. According to this embodiment, the influence of hemoglobin can be avoided efficiently.

Further, the reagent preferably further comprises a color developer, and the color developer is preferably a tetrazolium salt. According to these embodiments, it is possible to quantitatively determine a slight amount of component with a high sensitivity.

Further, the electron acceptor is preferably NAD or NADP. According to this embodiment, the influence caused by the change of absorption wavelength of hemoglobin can be avoided.

DETAILED DESCRIPTION OF THE INVENTION

For the biological specimen which is applicable in the present invention, several body fluids which may contain hemoglobin with higher possibility, for example blood, plasma, serum, urine may be included.

Further, the specific component which is contained in the biological specimen and to be subjected to measurement is not particularly limited so long as an enzyme which has an ability of oxidizing the specific component by the dehydrogenation in the presence of an electron acceptor is applicable to the specific component; or an enzyme which has an ability of oxidizing a substance derived from the specific component by the dehydrogenation in the presence of an electron acceptor is applicable to the substance.

For example, glucose, cholesterol, HDL-C, LDL-C, urea nitrogen, uric acid, neutral fat and the like may be mentioned. Particularly, the present invention is suitably applicable when a slight amount of the component e.g. mannose, 1,5-anhydroglucitol, arabinitol, inositol, sorbitol, fructose, galactose, bile acid, 3-deoxyglucosone, alcohol or the like for which a high sensitive detection is required, is quantitatively determined.

The enzyme used in the present invention is not particularly limited as long as it is an enzyme which has an ability of oxidizing a specific component or a substance derived from the specific component, as the object of measurement, by the dehydrogenation in the presence of an electron acceptor (hereinafter referred to as dehydrogenase). Namely, the enzyme of the present invention is not limited to an enzyme which directly reacts with the specific component, and a dehydrogenase for a substance quantitatively derived from the specific component by enzyme coupling system or the like may also be used. For example, when the specific component is glucose, glucose dehydrogenase which directly reacts with the glucose is preferably used. However, a dehydrogenase for glucose-6-phosphate which is formed by reacting the glucose with hexokinase which undergoes phosphorylation (glucose-6-phosphate dehydrogenase), or the like may be used. Here, with respect to the rest of the above-mentioned specific components, not only the enzyme which directly reacts with the specific component, but also a dehydrogenase for a substance quantitatively derived from the specific component by enzyme coupling system or the like may be used As these enzyme and dehydrogenase, well-known enzymes may be used.

Further, the electron acceptor is not particularly limited so long as the formed reductant of the electron acceptor can be directly quantitatively determined, or the reductant can be measured by colorimetry with a color developer. Specifically, for example, coenzyme such as NAD and NADP, phenazine methosulfates, dichlorophenol indophenol, ferricyanides and the like may preferably be mentioned. Among them, NAD and NADP are particularly preferably used.

Further, as the color developer, tetrazolium or its salts may preferably be mentioned. Specifically, nitrotetrazolium blue, 2-(4-iodophenyl)-3-(4-nitrophenyl)-5-phenyl-2H tetrazolium chloride, 3-(4,5-dimethyl-2-thiazolyl)-2,5-diphenyl-2H tetrazolium bromide, 2-(4-iodophenyl)-3-(4-nitrophenyl)-5-(2,4-disulfophenyl)-2H tetrazolium salt (hereinafter abbreviated as WST-1) and the like may be used. These are available, for example, from Dojindo Laboratories.

Hereinbelow, the quantitative determination method of the present invention will be explained with reference to preferred embodiments Here, "%" means "weight to weight percentage", unless otherwise specified.

The quantitative determination method of the present invention is a method for quantitatively determining a specific component in a biological specimen, which comprises reacting a biological specimen, in the presence of an electron acceptor, with an enzyme which has an ability, by the dehydrogenation reaction, to oxidize the specific component in a biological specimen or a substance derived from the specific component, and measuring the formed reductant of the electron acceptor, wherein a measuring reagent containing albumin is used.

Accordingly, basic operations of the quantitative determination method are carried out in accordance with known methods.

In the present invention, the concentration of albumin in the measuring reagent varies depending upon the origin of the albumin used, the hemoglobin content in the specimen, the albumin content originally contained in the specimen, and the like. Namely, the concentration of albumin in the measuring reagent is not generically determined, and its optimum concentration may be determined appropriately depending upon the respective specimens. For example, when albumin derived from human is used preferably 0.4 to 5% in usual, more preferably 0.6 to 2% of the albumin is contained in the measuring reagent. Further, when albumin derived from bovine is used, preferably 1 to 10%, more preferably 2.5 to 10% of the albumin is contained in the measuring reagent.

And, albumin, an electron acceptor, and a dehydrogenase which reacts with a specific component to be measured or a substance derived from the specific component to be measured, are added as the reagent, and enzyme reaction is carried out in an appropriate buffer solution (for example, phosphate buffer solution, glycine buffer solution, Tris-HCl buffer solution, Good's buffer solution, borate buffer solution, etc.), and then the formed reductant of the electron acceptor is quantitatively determined.

The addition concentration of the electron acceptor may appropriately be determined depending upon the type thereof. Further, the dehydrogenase may be added in such an amount that it will sufficiently react with the specific component in the specimen, and the addition concentration of the dehydrogenase may appropriately be determined depending upon the type or the like of the enzyme used.

In the present invention, as the method for quantitatively determining the reductant of the electron acceptor, the reductant of the electron acceptor may be directly quantitatively determined. However, in view of the sensitivity or the like, the reductant is preferably measured by colorimetry with a color developer. Specifically, it is preferable that NAD or NADP is used as the electron acceptor, and its reductant i.e. NADH or NADPH is reacted with a tetrazolium salt and diaphorase, and then the formed formazan is subjected to colorimetry.

The reagent for quantitative determination of the present invention is constituted so that the quantitative determination of a specific component in a biological specimen will be conveniently conducted. The reagent contains at least albumin, an electron acceptor and a dehydrogenase. It preferably further contains a color developer, and as the case requires, further contains an electron carrier such as diaphorase or phenazine methosulfate or the like.

The reagent for quantitative determination of the present invention is preferably comprised of two reagents for convenience.

EXAMPLES

Hereinbelow, the present invention will be specifically explained with reference to examples when the specific component in the biological specimen is mannose. However, it should be mentioned that the present invention is by no means restricted to them. Here, albumin used in the following examples was albumin derived from human (product number "A-1653", manufactured by Sigma) and albumin derived from bovine (heat treated, manufactured by Intergen Company). Further, as the enzyme which has an ability of oxidizing mannose by the dehydrogenation in the presence of an electron acceptor, aldohexose dehydrogenase obtained by purification from microorganisms which belong to *gluconobactor* genus, was used, and as the case requires, a glucose eliminating system was combined (reference may be made to JP-A-2001-197900).

Example 1

Using a coenzyme NADP as an electron acceptor and aldohexose dehydrogenase as a dehydrogenase, reagents for quantitative determination each comprising a first reagent and a second reagent were prepared. Here, first reagents were prepared so that the concentration of human serum albumin (HSA) would be 0, 0.5, 0.75 and 1.0%, respectively.

First reagent:

| First reagent: | |
|---|---|
| Borate buffer solution | 25 mM (pH 8.0) |
| Tween 20 | 1.3% |
| Human serum albumin (HSA) | 0 to 1.0% |

-continued

| Second reagent: | |
|---|---|
| Borate buffer solution | 25 mM (pH 8.0) |
| NADP | 4 mM |
| Aldohexose dehydrogenase | 70 U/mL |

And, a mannose aqueous solution (25 μg/mL) was mixed with hemoglobin at a ratio of 9:1. Then measurement specimens were prepared so that the hemoglobin concentration would be 0, 125, 250 and 500 mg/dL, respectively. The mannose concentration was measured with the above reagents. For the calibration curve, at the concentration of 0 and 10 μg/mL mannose solutions were used.

Specifically, 240 μL of the first reagent was added to each of 8 μL measurement specimen, and these were reacted at 37° C. for 5 minutes. Then, 60 μL of the second reagent was added thereto, and these were likewise reacted at 37° C. for 5 minutes. The absorbance was measured by 2-point assay with two wavelengths of a main wavelength of 340 nm and a sub wavelength of 700 nm. These operations were conducted with Hitachi 7150 Model Automatic analyzer. The results are indicated in Table 1.

TABLE 1

| Hemoglobin content (mg/dL) | HSA concentration (%) in the first reagent | | | |
|---|---|---|---|---|
| (Mannose 25 μg/mL) | 0 | 0.5 | 0.75 | 1 |
| 0 | 24.8 | 24.6 | 25.1 | 24.3 |
| 125 | 13.4 | 25.3 | 24.9 | 24.4 |
| 250 | 5.6 | 24.9 | 23.7 | 24.3 |
| 500 | 4.7 | 21.7 | 20.5 | 24.6 |

(Mannose; μg/mL)

From Table 1, it is found that influence of hemoglobin can be avoided and mannose can be quantitatively determined accurately by adding HSA.

Example 2

Using the same reagents and measurement specimens as used in the first reagent of Example 1 except that bovine serum (BSA) in place of HSA was used at a concentration of 0, 1.0, 3.0 or 5.0%, mannose was quantitatively determined. The results are indicated in Table 2.

TABLE 2

| Hemoglobin content (mg/dL) | BSA concentration (%) in the first reagent | | | |
|---|---|---|---|---|
| (Mannose 25 μg/mL) | 0 | 1 | 3 | 5 |
| 0 | 25.1 | 24.3 | 23.4 | 23.8 |
| 125 | 12.5 | 21.4 | 23.1 | 23 |
| 250 | 4.6 | 17.4 | 21.7 | 22.6 |
| 500 | 3.6 | 11 | 19.9 | 22.6 |

(Mannose; μg/mL)

From Table 2, it is found that influence of hemoglobin can be avoided and mannose can be quantitatively determined accurately by adding BSA. It is also found that the influence of hemoglobin can be avoided by HSA at a lower concentration as compared with BSA.

Example 3

Using a coenzyme NADP as an electron acceptor, WST-1 as a reductive color developer, aldohexose dehydrogenase as a dehydrogenase and diaphorase as an electron carrier, reagents for quantitative determination each comprising a first reagent and a second reagent were prepared. Here, first reagents were prepared so that the concentration of human serum albumin (HSA) would be 0, 0.5, 0.75 and 1.0%, respectively.

| First reagent: | |
|---|---|
| Borate buffer solution | 25 mM (pH 8.0) |
| WST-1 | 0.78 mM |
| Diaphorase | 6.4 U/mL |
| Tween 20 | 1.3% |
| Glucokinase | 4 U/mL |
| ATP | 13 mM |
| Magnesium acetate | 4 mM |
| Human serum albumin (HSA) | 0 to 1.0% |
| Second reagent: | |
| Borate buffer solution | 25 mM (pH 8.0) |
| NADP | 4 mM |
| Aldohexose dehydrogenase | 70 U/mL |

And, the serum was mixed with hemoglobin at a ratio of 9:1. Then measurement specimens were prepared so that the hemoglobin concentration would be 0, 125, 250 and 500 mg/dL, respectively. The mannose concentration was measured with the above reagents. For the calibration curve, at the concentration of 0 and 10 μg/mL mannose solutions were used.

Specifically, 240 μL of the first reagent was added to each of 8 μL serum specimen, and these were reacted at 37° C. for 5 minutes. Then, 60 μL of the second reagent was added thereto, and these were likewise reacted at 37° C. for 5 minutes. The absorbance was measured by 2-point assay with two wavelengths of a main wavelength of 450 nm and a sub wavelength of 700 nm. These operations were conducted with Hitachi 7150 Model Automatic analyzer. The results are indicated in Table 3.

TABLE 3

| Hemoglobin content | HSA concentration (%) in the first reagent | | | |
|---|---|---|---|---|
| (mg/dL) | 0 | 0.5 | 0.75 | 1 |
| 0 | 11.7 | 11.3 | 11.6 | 12.2 |
| 125 | 5.1 | 11.5 | 11.8 | 12.3 |
| 250 | 1.7 | 10.9 | 11.7 | 12.3 |
| 500 | 1.6 | 8.2 | 11.4 | 12.4 |

(Mannose; μg/mL)

From Table 3, it is found that influence of hemoglobin can be avoided and mannose can be quantitatively determined accurately by adding HSA.

Example 4

Using the same reagents and measurement specimens as used in the first reagent of Example 3 except that bovine serum albumin (BSA) was used at a concentration of 0, 1.0, 3.0 or 5.0%, mannose was quantitatively determined. The results are indicated in Table 4.

TABLE 4

| Hemoglobin content | HSA concentration (%) in the first reagent | | | |
|---|---|---|---|---|
| (mg/dL) | 0 | 1 | 3 | 5 |
| 0 | 11.7 | 12.4 | 12.6 | 12.9 |
| 125 | 5.1 | 12.1 | 12.9 | 13.9 |
| 250 | 1.7 | 5.4 | 9.7 | 12.7 |
| 500 | 1.6 | 3.8 | 8.2 | 13.1 |

(Mannose; μg/mL)

From Table 4, it is found that influence of hemoglobin can be avoided and mannose can be quantitatively determined accurately by adding BSA. It is also found that, the influence of hemoglobin can be avoided by HSA at a lower concentration as compared with BSA.

According to this invention, a measuring reagent containing albumin makes it possible to avoid the influence of hemoglobin if any contained in the specimen, wherein the biological specimen, in the presence of an electron acceptor, is reacted with an enzyme which has an ability, by the dehydrogenation reaction, to oxidize the specific component or a substance derived from the specific component in the biological specimen and the formed reductant of the electron acceptor is measured, thereby making a quantitative determination of target component in the specimen accurately.

What is claimed is:

1. A method for avoiding influence of hemoglobin in quantitatively determining a specific component in a biological specimen, which comprises:

reacting the biological specimen with a first reagent comprising albumin, then reacting the biological specimen with a second reagent in the presence of an electron acceptor, wherein the second reagent comprises a dehydrogenase which oxidizes the specific component or a substance derived from the specific component, wherein during the reacting with the second reagent the electron acceptor forms a reductant, and then measuring the reductant of the electron acceptor, wherein the first reagent comprising albumin is used to avoid the influence of hemoglobin.

2. The method for quantitatively determining a specific component in a biological specimen according to claim 1, wherein the albumin is derived from human or bovine.

3. The method for quantitatively determining a specific component in a biological specimen according to claim 1, wherein the measuring is carried out with a color developer for the electron acceptor.

4. The method for quantitatively determining a specific component in a biological specimen according to claim 3, wherein the color developer is a tetrazolium salt.

5. The method for quantitatively determining a specific component in a biological specimen according to claim 1, wherein the reductant of the electron acceptor is NADH or NADPH.

* * * * *